United States Patent

Kawasaki et al.

Patent Number: 6,166,221
Date of Patent: Dec. 26, 2000

[54] PRODUCTION METHOD OF OPTICALLY ACTIVE IMIDAZOLE COMPOUND, SYNTHETIC INTERMEDIATE THEREFOR AND PRODUCTION METHOD THEREOF

[75] Inventors: Kazuyuki Kawasaki; Haruhito Kobayashi; Syuji Ehara; Hideaki Sato, all of Chikujo-gun, Japan

[73] Assignee: Yoshitomi Pharmaceutical Industries, Ltd., Osaka, Japan

[21] Appl. No.: 09/511,782

[22] Filed: Feb. 23, 2000

Related U.S. Application Data

[62] Division of application No. 09/355,096, filed as application No. PCT/JP98/00150, Jan. 14, 1998, Pat. No. 6,066,739.

[30] Foreign Application Priority Data

Jan. 23, 1997 [JP] Japan ................................ 9-10114

[51] Int. Cl.[7] ............................................. C07D 233/60
[52] U.S. Cl. ................................................ 548/343.5
[58] Field of Search ........................................... 548/343.5

[56] References Cited

U.S. PATENT DOCUMENTS

| | | | |
|---|---|---|---|
| 6,066,739 | 5/2000 | Kawasaki et al. | 548/343.5 |
| 6,069,251 | 5/2000 | Thurkauf et al. | 544/295 |

FOREIGN PATENT DOCUMENTS

| | | |
|---|---|---|
| 57-70884 | 5/1982 | Japan . |
| 2-215771 | 8/1990 | Japan . |

OTHER PUBLICATIONS

Tsuruta et al., "Preparation of optically . . . diastereoisomeric esters," CA 114:101990 (Aug. 1990).

Primary Examiner—Joseph K. McKane
Assistant Examiner—Sonya Wright
Attorney, Agent, or Firm—Winderoth, Lind & Ponack, L.L.P.

[57] ABSTRACT

The present invention provides a method for producing an optically active 4-[α-hydroxy-5-(1-imidazolyl)-2-methylbenzyl]-3,5-dimethylbenzoic acid or a pharmaceutically acceptable salt thereof, which includes subjecting a compound of the formula (I)

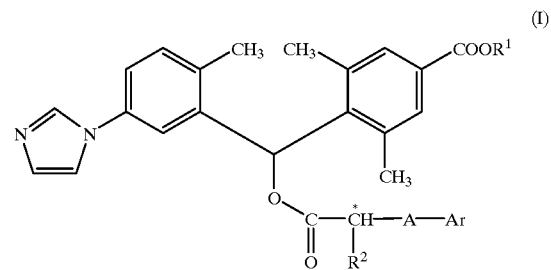

wherein each symbol in the formula is as defined in the specification, to optical resolution by fractional crystallization to give an optically active compound thereof and subjecting the compound to hydrolysis reaction. According to this method, a resolution method useful for industrial large-scale production of the optically active compound of 4-[α-hydroxy-5-(1-imidazolyl)-2-methylbenzyl]-3,5-dimethylbenzoic acid, which is useful as a thromboxane synthetase inhibitor and an agent for the prophylaxis and treatment of diabetic complications, can be obtained.

10 Claims, No Drawings

PRODUCTION METHOD OF OPTICALLY ACTIVE IMIDAZOLE COMPOUND, SYNTHETIC INTERMEDIATE THEREFOR AND PRODUCTION METHOD THEREOF

This is a divisional of Ser. No. 09/355,096, now U.S. Pat. No. 6,066,739 filed Jul. 23, 1999, which is a 371 of PCT/JP98/00150, filed Jan. 14, 1998.

TECHNICAL FIELD

The present invention relates to a method for producing an optically active imidazole compound, namely, an optically active 4-[α-hydroxy-5-(1-imidazolyl)-2-methylbenzyl]-3,5-dimethylbenzoic acid, which is useful as a thromboxane synthetase inhibitor and an agent for the prophylaxis and treatment of diabetic complications, a synthetic intermediate therefor and a production method thereof.

BACKGROUND ART

Japanese Patent Examined Publication No.41143/1993 discloses that 4-[α-hydroxy-5-(1-imidazolyl)-2-methylbenzyl]-3,5-dimethylbenzoic acid and pharmaceutically acceptable salts thereof have pharmacological actions such as potent TXA2 biosynthesis inhibitory action, platelet aggregation inhibitory action and vasodilating action, and that they are useful for the prophylaxis and treatment of thrombosis, cerebral apoplexy, myocardial infarction, acute heart death, angina pectoris, hypertension, asthma, nephiltis and the like. In addition, 4-[α-hydroxy-5-(1-imidazolyl)-2-methylbenzyl]-3,5-dimethylbenzoic acid, an optically active compound thereof and a pharmaceutically acceptable salt thereof have been found to be useful for the prophylaxis and treatment of diabetic complications, such as diabetic neuropathy, nephropathy, ophthalmopathy and arteriosclerosis (Japanese Patent Application No.340161/1995).

This pharmaceutically useful 4-[α-hydroxy-5-(1-imidazolyl)-2-methylbenzyl]-3,5-dimethylbenzoic acid has an asymmetric carbon in the molecular structure. When a compound having an asymmetric carbon is developed as a pharmaceutical agent, the corresponding optically active compound is used in view of provision of a chemically pure compound, reinforcement of pharmacological activity, removal of side effect, lowering of toxicity, simplification of absorption, metabolism, distribution and excretion, improvement in solubility and the like. This in turn renders resolution of the optical isomer an important matter for the development of a compound having an asymmetric carbon as a pharmaceutical agent.

As a method for resolving the optical isomer of 4-[α-hydroxy-5-(1-imidazolyl)-2-methylbenzyl]-3,5-dimethylbenzoic acid, Japanese Patent Unexamined Publication No. 215771/1990 discloses a method for resolving the optical isomer of 4-[α-hydroxy-5-(1-imidazolyl)-2-methylbenzyl]-3,5-dimethylbenzoic acid, which comprises ester-bonding hydroxyl group bonded to the asymmetric carbon of 4-[α-hydroxy-5-(1-imidazolyl)-2-methylbenzyl]-3,5-dimethylbenzoate and an optically pure chiral carboxylic acid compound, to give two kinds of diastereomers, subjecting the diastereomers to column chromatography and then to hydrolysis reaction.

However, this optical resolution by column chromatography requires a large amount of a filler, a large amount of a solvent and a large separation device for the small amount of a substance to be resolved. This method is effective for the separation of a trace amount, but when operability and cost are taken into consideration, is unsuitable for industrial scale mass production.

Therefore, there has been a demand for a practical and useful method for the resolution of the optical isomer of 4-[α-hydroxy-5-(1-imidazolyl)-2-methylbenzyl]-3,5-dimethylbenzoic acid.

DISCLOSURE OF THE INVENTION

To solve the above-mentioned problems, the present inventors have conducted various studies of a method for optical resolution by fractional crystallzation utilizing the difference in physical properties between two kinds of diastereomers generated by ester-bonding a hydroxyl group bonded to an asymmetric carbon and an optically pure chiral carboxylic acid compound, in an attempt to provide a method for industrial production of an optically active 4-[α-hydroxy-5-(1-imidazolyl)-2-methylbenzyl]-3,5-dimethylbenzoic acid in a large amount, and completed the present invention.

Accordingly, the present invention provides the following.

(1) A compound of the formula (I)

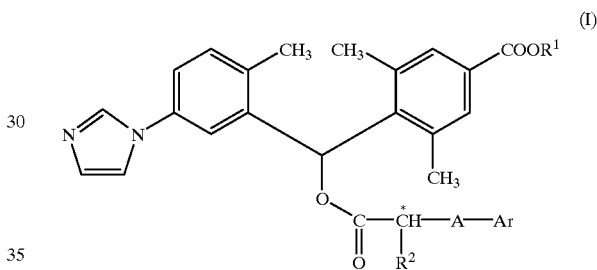

wherein $R^1$ is a lower alkyl, a phenylalkyl or a substituted phenylalkyl;

$R^2$ is a lower alkyl, a phenylalkyl or a substituted phenylalkyl;

Ar is a phenyl, a substituted phenyl, a naphthyl, a substituted naphthyl, a thienyl, a substituted thienyl, a furyl, a substituted furyl, a pyridyl or a substituted pyridyl;

A is a single bond or —$NHSO_2$—; and the carbon atom marked with * shows (S)— or (R)—, an optically active compound thereof or a pharmaceutically acceptable salt thereof.

(2) A method for producing an optically active 4-[α-hydroxy-5-(1-imidazolyl)-2-methylbenzyl]-3,5-dimethylbenzoic acid of the formula (II)

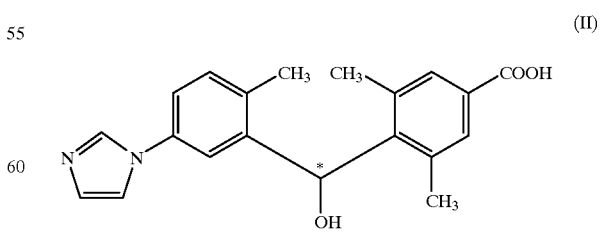

wherein carbon atom marked with * shows (S)— or (R)—, or a pharmaceutically acceptable salt thereof, which comprises subjecting a compound of the formula (I)

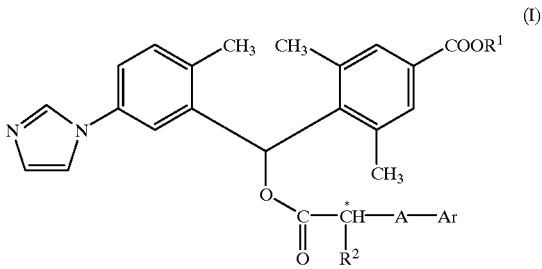

(I)

wherein $R^1$ is a lower alkyl, a phenylalkyl or a substituted phenylalkyl;

$R^2$ is a lower alkyl, a phenylalkyl or a substituted phenylalkyl;

Ar is a phenyl, a substituted phenyl, a naphthyl, a substituted naphthyl, a thienyl, a substituted thienyl, a furyl, a substituted furyl, a pyridyl or a substituted pyridyl;

A is a single bond or —NHSO$_2$—; and the carbon atom marked with * shows (S)— or (R)—, to optical resolution by fractional crystallization to give an optically active compound thereof and subjecting the obtained optically active compound to a hydrolysis reaction.

(3) A method for producing a compound of the formula (I)

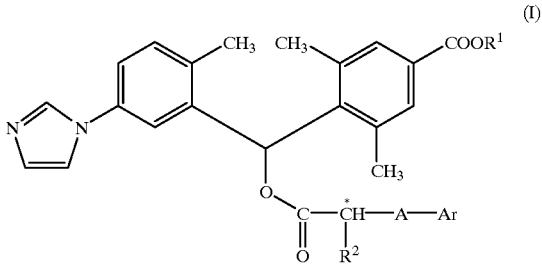

(I)

wherein $R^1$ is a lower alkyl, a phenylalkyl or a substituted phenylalkyl;

$R^2$ is a lower alkyl, a phenylalkyl or a substituted phenylalkyl;

Ar is a phenyl, a substituted phenyl, a naphthyl, a substituted naphthyl, a thienyl, a substituted thienyl, a furyl, a substituted furyl, a pyridyl or a substituted pyridyl;

A is a single bond or —NHSO$_2$—; and the carbon atom marked with * shows (S)— or (R)—, which comprises reacting a compound of the formula (III)

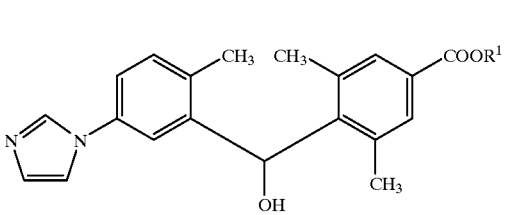

(III)

wherein $R^1$ is a lower alkyl, a phenylalkyl or a substituted phenylalkyl, and a compound of the formula (IV)

(IV)

wherein $R^2$ is a lower alkyl, a phenylalkyl or a substituted phenylalkyl;

Ar is a phenyl, a substituted phenyl, a naphthyl, a substituted naphthyl, a thienyl, a substituted thienyl, a furyl, a substituted furyl, a pyridyl or a substituted pyridyl;

A is a single bond or —NHSO$_2$—; and the carbon atom marked with * shows (S)— or (R)—, or reactive derivative thereof.

Of the compounds of the formula (I) in the present invention, ① a compound wherein $R^1$ is a lower alkyl, ② a compound wherein Ar is a phenyl, a substituted phenyl, a naphthyl or a substituted naphthyl, particularly, ③ a compound wherein $R^1$ is a lower alkyl, $R^2$ is a lower alkyl, a phenylalkyl or a substituted phenylalkyl, Ar is a phenyl, a substituted phenyl, a naphthyl or a substituted naphthyl and A is a single bond or —NHSO$_2$—, is preferable.

Specifically, the present invention relates to the compound of (1) above, an optically active compound thereof or a pharmaceutically acceptable salt thereof, and the production method of (2)-(3) above wherein the compound of the formula (I) is methyl (±)-4-[5-(1-imidazolyl)-α-{(S)-2-(6-methoxy-2-naphthyl)propionyloxy}-2-methylbenzyl]-3,5-dimethylbenzoate, methyl (S)-4-[5-(1-imidazolyl)-α-{(S)-2-(6-methoxy-2-naphthyl)propionyloxy}-2-methylbenzyl]-3,5-dimethylbenzoate, methyl (R)-4-[5-(1-imidazolyl)-α-{(S)-2-(6-methoxy-2-naphthyl)propionyloxy}-2 methylbenzyl]-3,5-dimethylbenzoate, methyl (±)-4-[5-(1-imidazolyl)-α-{(S)-2-(4-chlorobenzenesulfonylamino)propionyloxy}-2-methylbenzyl]-3,5-dimethylbenzoate, methyl (S)-4-[5-(1-imidazolyl)-α-{(S)-2-(4-chlorobenzenesulfonylamino)propionyloxy}-2-methylbenzyl]-3,5-dimethylbenzoate, methyl (±)-4-[5-(1-imidazolyl)-2-methyl-α-{(S)-2-(4-methylbenzenesulfonylamino)-3-phenylpropionyloxy}benzyl]-3,5-dimethylbenzoate, methyl (S)-4-[5-(1-imidazolyl)-2-methyl-α-{(S)-2-(4-methylbenzenesulfonylamino)-3-phenylpropionyloxy}benzyl]-3,5-dimethylbenzoate, methyl (±)-4-[5-(1-imidazolyl)-2-methyl-α-{(S)-2-(4-methylbenzenesulfonylamino)propionyloxy}benzyl]-3,5-dimethylbenzoate, or methyl (S)-4-[5-(1-imidazolyl)-2-methyl-α-{(S)-2-(4-methylbenzenesulfonylamino)propionyloxy}benzyl]-3,5-dimethylbenzoate.

In the present specification, lower alkyl at $R^1$ is alkyl having 1 to 4 carbon atoms, such as methyl, ethyl, propyl, isopropyl, butyl, isobutyl, tert-butyl and the like, with preference given to methyl.

Phenylalkyl at $R^1$ is phenylalkyl wherein the alkyl moiety has 1 to 4 carbon atoms, such as benzyl, 2-phenylethyl, 3-phenylpropyl, 4-phenylbutyl and the like.

The substituted phenylalkyl at $R^1$ is phenylalkyl having the same or different, 1 to 3 substituents selected from halogen (e.g., fluorine, chlorine, bromine, iodine), lower alkyl (same as lower alkyl at $R^1$ above), lower alkoxy (e.g., methoxy, ethoxy, propoxy, isopropoxy, butoxy, tert-butoxy and the like), hydroxyl and nitro, on the benzene ring, with preference given to 2-chlorobenzyl.

Lower alkyl at $R^2$ is alkyl having 1 to 4 carbon atoms, such as methyl, ethyl, propyl, isopropyl, butyl, isobutyl, tert-butyl and the like, with preference given to methyl.

Phenylalkyl at $R^2$ is phenylalkyl wherein the alkyl moiety has 1 to 4 carbon atoms, and is exemplified by benzyl, 2-phenylethyl, 3-phenylpropyl, 4-phenylbutyl and the like, with preference given to benzyl.

The substituted phenylalkyl at $R^2$ is phenylalkyl having the same or different, 1 to 3 substituents selected from halogen (e.g., fluorine, chlorine, bromine, iodine), lower alkyl (same as lower alkyl at $R^1$ above), lower alkoxy (e.g., methoxy, ethoxy, propoxy, isopropoxy, butoxy, tert-butoxy and the like), hydroxyl and nitro, on the benzene ring, with preference given to 4-hydroxybenzyl.

The substituted phenyl at Ar is phenyl having the same or different, 1 to 3 substituents selected from halogen (e.g., fluorine, chlorine, bromine, iodine), lower alkyl (same as lower allyl at $R^1$ above), lower alkoxy (e.g., methoxy, ethoxy, propoxy, isopropoxy, butoxy, tert-butoxy and the like), and nitro, on the benzene ring, which is exemplified by 4-chlorophenyl, 4-methylphenyl, 3-nitrophenyl and the like, with particular preference given to 4-chlorophenyl and 4-methylphenyl.

Naphthyl at Ar is 1-naphthyl or 2-naphthyl, with preference given to 2-naphthyl.

The substituted naphthyl at Ar is naphthyl having the same or different, 1 to 3 substituents selected from halogen (e.g., fluorine, chlorine, bromine, iodine), lower alkyl (same as lower alkyl at $R^1$ above), lower alkoxy (e.g., methoxy, ethoxy, propoxy, isopropoxy, butoxy, tert-butoxy and the like) and nitro, on the naphthalene ring, with preference given to 6-methoxy-2-naphthyl.

Thienyl at Ar is 2-thienyl or 3-thienyl.

The substituted thienyl at Ar is thienyl having the same or different, 1 to 3 substituents selected from halogen (e.g., fluorine, chlorine, bromine, iodine), lower alkyl (same as lower alkyl at $R^1$ above), lower alkoxy (e.g., methoxy, ethoxy, propoxy, isopropoxy, butoxy, tert-butoxy and the like) and nitro, on the thiophene ring, which is exemplified by 5-chloro-2-thienyl and the like.

Furyl at Ar is 2-furyl or 3-furyl.

The substituted furyl at Ar is furyl having the same or different, 1 to 3 substituents selected from halogen (e.g., fluorine, chlorine, bromine, iodine), lower alkyl (same as lower alkyl at $R^1$ above), lower alkoxy (e.g., methoxy, ethoxy, propoxy, isopropoxy, butoxy, tert-butoxy and the like) and nirto, on the furan ring, which is exemplified by 5-chloro-2-furyl and the like.

Thienyl at Ar is 2-pyridyl, 3-pyridyl or 4-pyridyl.

The substituted pyridyl at Ar is pyridyl having the same or different, 1 to 3 substituents selected from halogen (e.g., fluorine, chlorine, bromine, iodine), lower alkyl (same as lower alkyl at $R^1$ above), lower alkoxy (e.g., methoxy, ethoxy, propoxy, isopropoxy, butoxy, tert-butoxy and the like) and nitro, on the pyridine ring, which is exemplified by 6-chloro-3-pyridyl and the like.

The pharmaceutically acceptable salt of the compound of the present invention is exemplified by salts with inorganic acids such as hydrochloric acid, hydrobromic acid, sulfuric acid and the like, or organic acids such as fumaric acid, maleic acid, mandelic acid, citric acid, tartaric acid, salicylic acid and the like; salts with metals such as sodium, potassium, lithium, calcium, magnesium, zinc, aluminum and the like; and salts with amino acids such as lysine, ornithine and the like. In addition, hydrates thereof (½ hydrate, monohydrate, dihydrate and the like) are also encompassed.

The method of the present invention is explained in detail in the following.

The diastereomer of the formula (I) can be synthesized by reacting a compound of the formula (III)

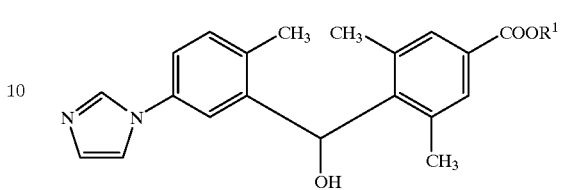

(III)

wherein $R^1$ is as defined above, which can be synthesized by the method disclosed in, for example, Japanese Patent Examined Publication No. 41143/1993, and a compound of the formula (IV)

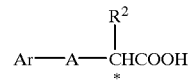

(IV)

wherein $R^2$, Ar and A are as defined above, or a reactive derivative thereof (e.g., acid halides, acid anhydrides, mixed acid anhydrides, active esters and the like).

The obtained diastereomer of the formula (I) is resolved into each optical isomer of the formula (I) by fractional crystallization and subjected to hydrolysis to give the objective optically active 4-[α-hydroxy-5-(1-imidazolyl)-2-methylbenzyl]-3,5-dimethylbenzoic acid of the formula (II).

The reaction of the compound of the formula (III) and the compound of the formula (IV) can be carried out using a dehydrating reagent used for ester synthesis, such as dicyclohexylcarbodiimide (where necessary, N-hydroxysuccinimide, 1-hydroxybenzotriazole, N-hydroxy-5-norbornene-2,3-dicarboximide and the like are added), carbonyldiimidazole, Vilsmeier reagent, tosylchloride-pyridine, phosphorus oxychloride, polyphosphoric acid, dimethylformamide diethyl acetal, Mukaiyama reagent, Mitsunobu reaction and the like. From industrial aspect, the compound of the formula (IV) is advantageously reacted with thionyl chloride to give a carboxylic acid chloride thereof and reacted with the compound of the formula (III). The compound of the formula (IV) can be led to the corresponding carboxylic acid chloride by reacting with thionyl chloride at room temperature or under reflux without solvent or in the presence of a solvent such as haloalkanes (e.g., chloroform, methylene chloride, dichloroethane and the like), benzene, toluene and the like. When the compound of the formula (IV) is acid halide, the reaction between the compound of the formula (III) and the compound of the formula (I proceeds in a suitable solvent (e.g., benzene, toluene, methylene chloride, dichloroethane, dimethylformamide and the like, or a mixed solvent thereof in the presence of a base (e.g., potassium carbonate, triethylamine, pyridine and the like) at 0–40° C. for 1–24 hours.

The obtained diastereomer of the formula (I) is resolved into each optical isomer of the formula (I) by fractional crystallization. The fractional crystallization can be performed in a suitable solvent such as methanol, ethanol, isopropyl alcohol, toluene, ethyl acetate, hexane, isopropyl ether, acetonitrile, dioxane, acetone and the like, or a mixed solvent thereof, depending on the objective isomer and the kind of substituents thereof. The hydrolysis of each optical isomer of the formula (I) obtained by the aforementioned fractional crystallization proceeds under any conditions as long as epimerization does not occur. Preferably, it proceeds in a suitable solvent (e.g., water, methanol, ethanol, dioxane and the like or a mixed solvent thereof) in the presence of an alkali metal hydroxide (e.g., sodium hydroxide, potassium hydroxide, lithium hydroxide) or an alkali metal salt (e.g., sodium carbonate, potassium carbonate) at room temperature to a temperature not more than the boiling point of the solvent used. It also proceeds under acidic conditions using hydrochloric acid, hydrobromic acid, sulfuric acid and the like.

The compound of the formula (I) thus obtained and an optically active 4-[α-hydroxy-5-(1-imidazolyl)-2-methylbenzyl]-3,5-dimethylbenzoic acid can be isolated and purified by a convenient method such as recrystallization and the like. Further, the corresponding salts can be obtained by treating with an inorganic acid such as hydrochloric acid, hydrobromic acid, sulfuric acid and the like; organic acid such as fumaric acid, maleic acid, mandelic acid, citric acid, tartaric acid, salicylic acid and the like; metal hydroxide such as sodium hydroxide, potassium hydroxide, lithium hydroxide, calcium hydroxide, magnesium hydroxide, zinc hydroxide, aluminum hydroxide and the like; or amino acid such as lysine, ornithine and the like.

Particularly, when a calcium salt, magnesium salt, zinc salt or aluminum salt is to be produced, the compound is once converted to the corresponding salt by the treatment with sodium hydroxide or potassium hydroxide and subjected to salt-exchange using metal chloride such as calcium chloride, magnesium chloride, zinc chloride and aluminum chloride and the like to give the corresponding salt.

The compound of the formula (I) thus obtained is exemplified by the following compounds. The present invention encompasses each of these diastereomers and diastereomeric mixtures thereof.

(1) Methyl 4-[5-(1-imidazolyl)-α-{(S)-2-(6-methoxy-2-naphthyl)propionyloxy}-2-methylbenzyl]-3,5-dimethylbenzoate [Examples 1 and 11: (S) compound and diastereomeric mixture thereof, Example 9: (R) compound]

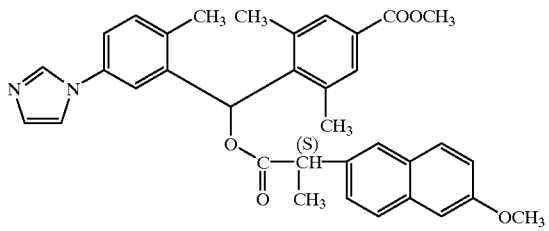

(2) Methyl 4-[5-(1-imidazolyl)-2-methyl-α-{(S)-2-phenylpropionyloxy}benzyl]-3,5-dimethylbenzoate

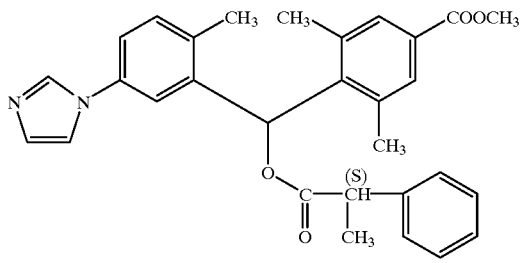

(3) 2-Chlorobenzyl 4-[5-(1-imidazolyl)-α-{(S)-2-(6-methoxy-2-naphthyl)-propionyloxy}-2-methylbenzyl]-3,5-dimethylbenzoate

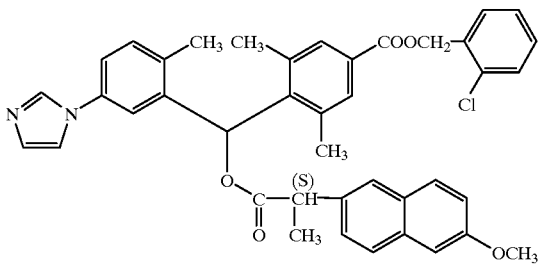

(4) Methyl 4-[5-(1-imidazolyl)-α-{(S)-2-(4-chlorobenzenesulfonylamino)propionyloxy}-2-methylbenzyl]-3,5-dimethylbenzoate [Example 3: (S) compound and diastereomeric mixture thereof]

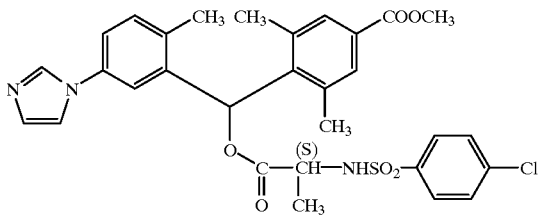

(5) Methyl 4-[5-(1imidazolyl)-2-methyl-α-{(S)-2-(4-methylbenzenesulfonylamino)-3-phenylpropionyloxy}benzyl]-3,5-dimethylbenzoate [Example 5: (S) compound and diastereomeric mixture thereof]

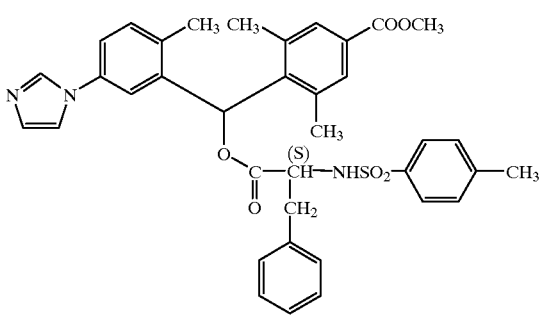

(6) Methyl 4-[5-(1-imidazolyl)-2-methyl-α-{(S)-2-(4-methylbenzenesulfonylamino)propionyloxy}benzyl]-3,5-dimethylbenzoate [Example 7: (S) compound and diastereomeric mixture thereof]

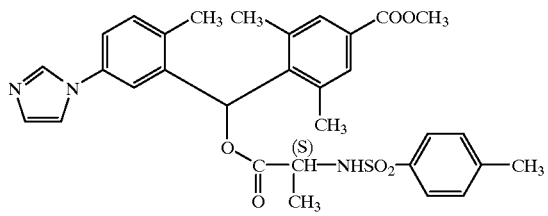

(7) Methyl 4-[5-(1-imidazolyl)-2-methyl-α-{(S)-2-(3-nitrobenzenesulfonylamino)propionyloxy}benzyl]-3,5-dimethylbenzoate

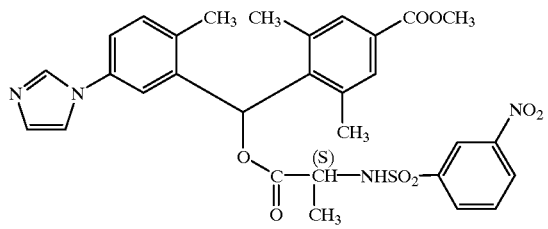

(8) Methyl 4-[5-(1-imidazolyl)-2-methyl-α-{(S)-2-(4-methylbenzenesulfonylamino)-4-methylpentanoyloxy}benzyl]-3,5-dimethylbenzoate

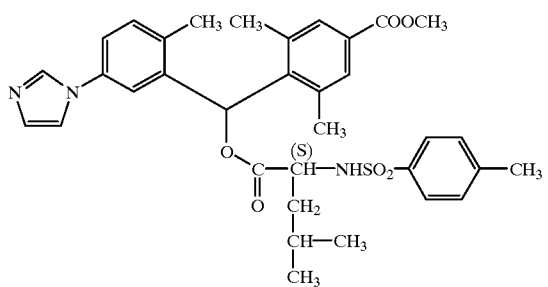

(9) Methyl 4-[5-(1-imidazolyl)-2-methyl-α-{(S)-2-(4-methylbenzenesulfonylamino)-3-methylbutyryloxy}benzyl]-3,5-dimethylbenzoate

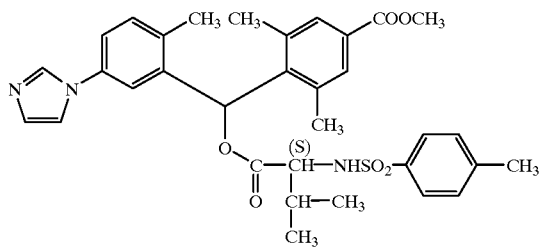

(10) Methyl 4-[5-(1-imidazolyl)-2-methyl-α-{(S)-2-(4-methylbenzenesulfonylamino)-3-(4-hydroxyphenyl)propionyloxy}benzyl]-3,5-dimethylbenzoate

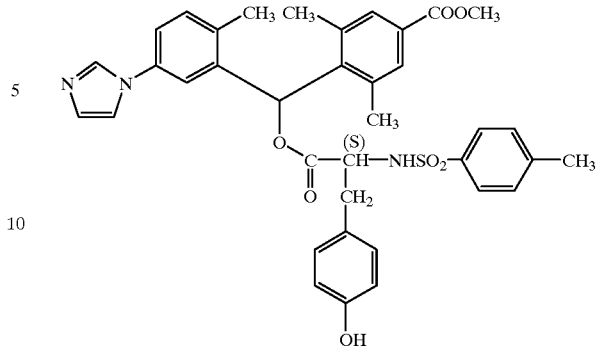

The compound of the formula (IV), which is an optically resolving agent in the present invention, may be a commercially available compound (for example, (S)-2-(6-methoxy-2-naphthyl)propionic acid and the like) or one synthesized by reacting an industrially available amino acid and phenylsulfonyl chloride, substituted phenylsulfonyl chloride, naphthylsulfonyl chloride, substituted naphthylsulfonyl chloride, thienylsulfonyl chloride, substituted thienylsulfonyl chloride, furylsulfonyl chloride, substituted furylsulfonyl chloride, pyridylsulfonyl chloride, substituted pyridylsulfonyl chloride and the like.

According to the method of the present invention described in the foregoing, the objective optically active 4-[α-hydroxy-5-(1-imidazolyl)-2-methylbenzyl]-3,5-dimethylbenzoic acid can be produced efficiently and in large amounts without suffering from the problems in the conventional methods.

The present invention is explained in detail in the following by way of Example, to which the present invention is not limited.

EXAMPLE 1

Methyl (±)-4-[α-hydroxy-5-(1-imidazolyl)-2-methylbenzyl]-3,5-dimethylbenzoate (70 g) was suspended in dimethylformamide (350 ml) and pyridine (23.7 ml), and a solution of (S)-2-(6-methoxy-2-naphthyl)propionyl chloride (59.7 g) in toluene (250 ml) was added dropwise to the suspension over 10 minutes with stirring under ice-cooling. The mixture was stirred at room temperature for 4 hours and poured into water (1400 ml). The precipitated oily substance was extracted with toluene and washed successively with 5% citric acid, 5% potassium carbonate and water. The organic layer was separated and dried over magnesium sulfate. The solvent was evaporated under reduced pressure to give 113 g of methyl(±)-4-[5-(1-imidazolyl)-α-{(S)-2-(6-methoxy-2-naphthyl)propionyloxy}-2-methylbenzyl]-3,5-dimethylbenzoate as a pale-yellow oil. This was crystallized from ethyl acetate (330 ml) and isopropyl ether (1300 ml) and the obtained crystals were recrystallized from isopropyl alcohol (300 ml) to give 47 g of methyl (S)-4-[5-(1-imidazolyl)-α-{(S)-2-(6-methoxy-2-naphthyl)propionyloxy}-2-methylbenzyl]-3,5-dimethylbenzoate as white crystals, melting point 156–158° C., optical rotation $[\alpha]_D^{24}$+87.3° (c=1, chloroform).

IR(KBr, cm$^{-1}$):3436,3118, 1714, 1508, 1307

$^1$H-NMR(CDCl$_3$) δ(ppm): 1.59(3H, d), 2.11(6H, s), 2.25 (3H, s), 3.90(3H, s), 3.92(3H, s), 3.854.00(1H, m), 6.80–7.70(15H, m)

EXAMPLE 2

Methyl (S)-4-[5-(1-imidazolyl)-α-{(S)-2-(6-methoxy-2-naphthyl)propionyloxy}-2-methylbenzyl]-3,5- dimethylbenzoate (47 g) obtained in Example 1 was suspended in methanol (376 ml) and an aqueous solution (95 ml) containing sodium hydroxide (8 g) was added, which was followed by stirring at 60° C. for 2 hours. The reaction mixture was concentrated and to the residue were added dimethylformamide (300 ml) and water (300 ml), which was followed by neutralization with glacial acetic acid (23 ml). The precipitated crystals were collected by filtration, washed with water and acetone, and recrystallized from dimethylformamide to give 25.3 g of (S)-4-[α-hydroxy-5-(1-imidazolyl)-2-methylbenzyl]-3,5-dimethylbenzoic acid, melting point 286–288° C. (decomposition), optical rotation $[\alpha]_D^{21}$ –261.5° (c=1.0, dimethylformamide).

IR (KBr, cm$^{-1}$): 3530, 2400, 1700, 1505

$^1$H-NMR (D$_2$O+NaOH)δ(ppm): 1.73(3H, s), 2.12(6H, s), 6. 10(1H, s), 6.90–7.80(8H, m)

The thus-obtained compound was suspended in water (150 ml). Sodium hydroxide (3 g) was added and the mixture was stirred. The insoluble matter was filtered off and an aqueous solution (40 ml) containing anhydrous calcium chloride (4.2 g) was added. The precipitated crystals were collected by filtration and dried to give the corresponding calcium salt as a white powder, optical rotation $[\alpha]_D^{24}$ –136.7° (c=0.3. H$_2$O)

IR (KBr, cm$^{-1}$): 3394, 1594, 1544, 1508

$^1$H-NMR (DMSO-d$_6$) δ(ppm): 1.89(3H, s), 2.18(6H, s), 5.94(1H, s), 6.09(1H, s), 7.08–8.09(8H, m)

EXAMPLE 3

Methyl (±)-4-[α-hydroxy-5-(1-imidazolyl)-2-methylbenzyl]-3,5-dimethylbenzoate (9.2 g) was suspended in dichloroethane (110 ml) and pyridine (3.15 ml), and a solution of (S)-2-(4-chlorobenzenesulfonylamino)propionyl chloride (8.9 g) in dichloroethane (25 ml) was added dropwise over 5 minutes with stirring under ice-cooling. The mixture was stirred at room temperature for 3 hours and the reaction mixture was washed successively with water, 5% citric acid, 5% potassium carbonate and water. The organic layer was separated and dried over magnesium sulfate. The solvent was evaporated under reduced pressure to give 15.7 g of methyl (±)4-[5-(1-imidazolyl)-α-{(S)-2-(4-chlorobenzenesulfonylamino)propionyloxy}-2-methylbenzyl]-3,5-dimethylbenzoate as a pale-yellow oil. This was crystallized from ethyl acetate (27 ml) and isopropyl ether (108 ml) and the obtained crystals were recrystallized from ethyl acetate (15 ml) and isopropyl ether (30 ml) to give 5.2 g of methyl (S)-4-[5-(1-imidazolyl)-α-{(S)-2-(4-chlorobenzenesulfonylamino)propionyloxy}-2-methylbenzyl]-3,5-dimethylbenzoate as white crystals, melting point 126–128° C.

$^1$H-NMR (CDCl$_3$) δ(ppm): 1.32(3H, d), 2.07(3H, s), 2.34(6H, s), 3.91(3H, s), 4.10–4.16(1H, m), 6.29(1H, d), 6.95–7.81(13H, m)

EXAMPLE 4

The compound obtained in Example 3 was treated in the same manner as in Example 2 to give 2.4 g of (S)-4-[α-hydroxy-5-(1-imidazolyl)-2-methylbenzyl]-3,5-dimethylbenzoic acid, melting point 286–288° C. (decomposition), optical rotation $[\alpha]_D^{21}$ –261.5° (c=1.0, dimethylformamide).

IR (KBr, cm$^{-1}$): 3530, 2400, 1700, 1505

$^1$H-NMR (D$_2$O+NaOH) δ(ppm): 1.73 (3H,s), 2.12(6H, s), 6.10(1H, s), 6.90–7.80(8H, m)

EXAMPLE 5

Methyl (±)-4-[α-hydroxy-5-(1-imidazolyl)-2-methylbenzyl]-3,5-dimethylbenzoate (46 g) was suspended in dichloroethane (550 ml) and pyridine (15.8 ml), and a solution of (S)-2-(4-methylbenzenesulfonylamino)-3-phenylpropionyl chloride (53.2 g) in dichloroethane (125 ml) was added dropwise to the suspension over 10 minutes with stirring under ice-cooling. The mixture was stirred at room temperature for 4 hours, and the reaction mixture was washed successively with water, 5% citric acid, 5% potassium carbonate and water. The organic layer was separated and dried over magnesium sulfate. The solvent was evaporated under reduced pressure to give 86 g of methyl (±)-4-[5-(1-imidazolyl)-2-methyl-α-{(S)-2-(4-methylbenzenesulfonylamino)-3-phenylpropionyloxy}-benzyl]-3,5-dimethylbenzoate as a pale-yellow oil. This was crystallized from ethyl acetate (150 mil) and isopropyl ether (600 ml) and the obtained crystals were recrystallized from ethyl acetate (75 ml) and isopropyl ether (150 ml) to give 29.8 g of methyl (S)-4-[5-(1-imidazolyl)-2-methyl-α-{(S)-2-(4-methylbenzenesulfonylamino)-3-phenylpropionyloxy}benzyl]-3,5-dimethylbenzoate as white crystals, melting point 111–112° C.

$^1$H-NMR (CDCl$_3$) δ(ppm): 2.03(3H, s), 2.30(6H, s), 2.37 (3H, s), 2.76–3.00(2H, m), 3.92(3H, s), 4.254.34(1H, m), 5.47(1H, d), 6.67–7.74(18H, m)

EXAMPLE 6

The compound obtained in Example 5 was treated in the same manner as in Example 2 to give 13.8 g of (S)-4-[α-hydroxy-5-(1-imidazolyl)-2-methylbenzyl]-3,5-dimethylbenzoic acid, melting point 286–288° C. (decomposition), optical rotation $[\alpha]_D^{21}$ –261.5° (c=1.0, dimethylformamide).

IR (KBr, cm$^-$): 3530, 2400, 1700, 1505

$^1$H-NMR (D$_2$O+NaOH) δ(ppm): 1.73(3H, s), 2.12(6H, s), 6.10(1H, s), 6.90–7.80(8H, m)

EXAMPLE 7

Methyl (±)-4-[α-hydroxy-5-(1-imidazolyl)-2-methylbenzyl]-3,5-dimethylbenzoate (35 g) was suspended in dichloroethane (350 ml) and pyridine (12 ml) and a solution of (S)-2-(4-methylbenzenesulfonylamino) propionyl chloride (31.4 g) in dichloroethane (70 ml) was added dropwise to the suspension over 10 minutes with stirring under ice-cooling. The mixture was stirred at room temperature for 4 hours, and the reaction mixture was washed successively with water, 5% citric acid, 5% potassium carbonate and water. The organic layer was separated and dried over magnesium sulfate. The solvent was evaporated under reduced pressure to give 58 g of methyl (±)-4-[5-(1-imidazolyl)-2-methyl-α-{(S)-2-(4-methylbenzenesulfonylamino)propionyloxy}benzyl]-3,5-dimethylbenzoate as a pale-yellow oil. This was crystallized from ethyl acetate (120 ml) and isopropyl ether (480 ml), and the obtained crystals were recrystallized from ethyl acetate (50 ml) and isopropyl ether (100 ml) to give 20 g of methyl (S)-4-[5-(1-imidazolyl)-2-methyl-α-{(S)-2-(4-methylbenzenesulfonylamino)propionyloxy}benzyl]-3,5-dimethylbenzoate as white crystals, melting point 103–105° C.

$^1$H-NMR (DMSO-d$_6$) δ(ppm): 1.13(3H, d), 2.08(3H, s), 2.31(6H, s), 2.32 (3H, s), 3.84(3H, s), 4.07–4.18(1H, m), 7.10–7.66(12H, m), 8.12(1H, s), 8.39(1H, d)

EXAMPLE 8

The compound obtained in Example 7 was treated in the same manner as in Example 2 to give 10.5 g of (S)-4-[α- hydroxy-5-(1-imidazolyl)-2-methylbenzyl]-3,5-dimethylbenzoic acid, melting point 286–288° C. (decomposition), optical rotation [α]$_D^{21}$–261.50 (c=1.0, dimethylformamide).

IR (KBr, cm$^{-1}$): 3530, 2400, 1700, 1505

$^1$H-NMR (D$_2$O+NaOH) δ(ppm): 1.73(3H, s), 2.12(6H, s), 6.10(1H, s), 6.90–7.80(8H, m)

EXAMPLE 9

Methyl (S)-4-[5-(1-imidazolyl)-α-{(S)-2-(6-methoxy-2-naphthyl)propionyloxy}-2-methylbenzyl]-3,5-dimethylbenzoate was crystallized from methyl (±)-4-[5-(1-imidazolyl)-α-{(S)-2-(6-methoxy-2-naphthyl)propionyloxy}-2-methylbenzyl]-3,5-dimethylbenzoate according to the method disclosed in Example 1. The obtained mother liquor was left standing in refrigerator for 2 days and the precipitated crystals were collected by filtration. The obtained crystals were recrystallized from isopropyl alcohol (200 ml) to give 35 g of methyl (R)-4-[5-(1-imidazolyl)-α-{(S)-2-(6-methoxy-2-naphthyl)propionyloxy}-2-methylbenzyl]-3,5-dimethylbenzoate as white crystals, melting point 115–117° C., optical rotation [α]$_D^{25}$–57.7° (c=1, chloroform).

IR (KBr, cm$^{-1}$): 2966, 1720, 1606, 1506, 1307

$^1$H-NMR (CDCl$_3$) δ(ppm): 1.57(3H, d), 1.85(3H, s), 2.35(6H, s), 3.92(3H, s), 3.94(3H, s), 3.89–3.97(1H, m), 6.66–7.73(15H, m)

EXAMPLE 10

Methyl (R)-4-[5-(1-imidazolyl)-α-{(S)-2-(6-methoxy-2-naphthyl)propionyloxy}-2-methylbenzyl]-3,5-dimethylbenzoate (35 g) obtained in Example 9 was suspended in methanol (280 ml) and an aqueous solution (70 ml) containing sodium hydroxide (6.2 g) was added, which was followed by sting at 60° C. for 2 hours. The reaction mixture was concentrated and to the residue were added dimethylformamide (210 ml) and water (210 ml), which was followed by neutralization with glacial acetic acid (17.5 ml). The precipitated crystals were collected by filtration, washed with water and acetone, and recrystallized from dimethylformamide to give 17.8 g of (R)-4-[α-hydroxy-5-(1-imidazolyl)-2-methylbenzyl]-3,5-dimethylbenzoic acid, melting point 286–288° C. (decomposition), optical rotation [α]D$^{21}$+260.5° (c=1.0, dimethylformamide).

IR (KBr, cm$^{-1}$): 3530, 2400, 1700, 1505

$^1$H-NMR (D$_2$O+NaOH) δ(ppm): 1.73(3H, s), 2.12(6H, s), 6.10(11H, s), 6.90–7.80(8H, m)

EXAMPLE 11

Methyl (±)-4-[α-hydroxy-5-(1-imidazolyl)-2-methylbenzyl]-3,5-dimethylbenzoate (70 g) was suspended in dimethylformamide (350 ml) and pyridine (23.7 ml) and a solution of (S)-2-(6-methoxy-2-naphthyl)propionyl chloride (59.7 g) in toluene (250 ml) was added dropwise to the suspension over 10 minutes with stirring under ice-cooling. The mixture was stirred at room temperature for 4 hours, poured into water (1400 ml), and the precipitated oily substance was extracted with toluene and washed successively with 5% citric acid, 5% potassium carbonate and water. The organic layer was separated and dried over magnesium sulfate. The solvent was evaporated under reduced pressure to give 113 g of methyl (±)-4-[5-(1-imidazolyl)-α-{(S)-2-(6-methoxy-2-naphthyl)propionyloxy}-2-methylbenzyl]-3,5-dimethylbenzoate as pale-yellow oil. This was crystallized from isopropyl alcohol (560 ml), and the obtained crystals were recrystallized from isopropyl alcohol (300 ml) to give 42 g of methyl (S)-4-[5-(1-imidazolyl)-α-{(S)-2-(6-methoxy-2-naphthyl)propionyloxy}-2-methylbenzyl]-3,5-dimethylbenzoate as white crystals, melting point 156–158° C., optical rotation [α]$_D^{24}$+87.3° (c=1, chloroform).

IR (KBr, cm$^{-1}$): 3436, 3118, 1714, 1508, 1307

$^1$H-NMR (CDCl$_3$) δ(ppm): 1.59(3H, d), 2.11(6H, s), 2.25(3H, s), 3.90(3H, s), 3.92(3H, s), 3.85–4.00(1H, m), 6.80–7.70(15H, m)

This application is based on application No. 10114/1997 filed in Japan, the content of which is incorporated hereinto by reference.

What is claimed is:

1. A compound of the formula (I)

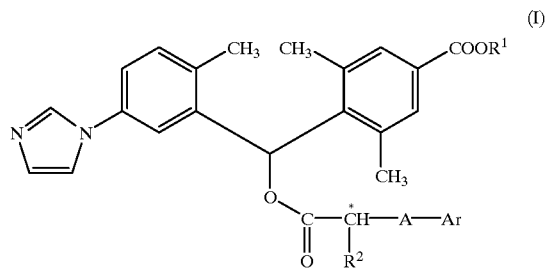

wherein $R^1$ is a lower alkyl, a phenylalkyl or a substituted phenylalkyl;

$R^2$ is a lower alkyl, a phenylalkyl or a substituted phenylalkyl;

Ar is a phenyl, a substituted phenyl, a naphthyl, a substituted naphthyl, a thienyl, a substituted thienyl, a furyl, a substituted furyl, a pyridyl or a substituted pyridyl;

A is a single bond or —NHSO$_2$—; and the carbon atom marked with * shows (S)— or (R)—, an optically active compound thereof or a pharmaceutically acceptable salt thereof.

2. The compound of claim 1, wherein, in the formula (I), $R^1$ is a lower alkyl, an optically active compound thereof or a pharmaceutically acceptable salt thereof.

3. The compound of claim 1, wherein, in the formula (I), Ar is a phenyl, a substituted phenyl, a naphthyl or a substituted naphthyl, an optically active compound thereof or a pharmaceutically acceptable salt thereof.

4. The compound of claim 1, wherein, in the formula (I), $R^1$ is a lower alkyl, $R^2$ is a lower alkyl, a phenylalkyl or a substituted phenylalkyl, Ar is a phenyl, a substituted phenyl, a naphthyl or a substituted naphthyl, and A is a single bond or —NHSO$_2$—, an optically active compound thereof or a pharmaceutically acceptable salt thereof.

5. The compound of claim 1, which is a member selected from the group consisting of methyl (±)-4-[5-(1-imidazolyl)-α-{(S)-2-(6-methoxy-2-naphthyl)propionyloxy}-2-methylbenzyl]-3,5-dimethylbenzoate, methyl (S)-4-[5-(1-imidazolyl)-α-{(S)-2-(6-methoxy-2-naphthyl)propionyloxy}-2-methylbenzyl]-3,5-dimethylbenzoate, methyl (R)-4-[5-(1-imidazolyl)-α-{(S)-2-(6-methoxy-2-naphthyl)propionyloxy}-2-methylbenzyl]-3,5-dimethylbenzoate, methyl (±)-4-[5-(1-imidazolyl)-α-{(S)-2-(4-chlorobenzenesulfonylamino)propionyloxy}-2-methylbenzyl]-3,5-dimethylbenzoate, methyl (S)-4-[5-(1-imidazolyl)-α-{(S)-2-(4-chlorobenzenesulfonylamino)propionyloxy}-2-methylbenzyl]-3,5-dimethylbenzoate, methyl (±)-4-[5-(1-imidazolyl)-2-methyl-α-{(S)-2-(4-methylbenzenesulfonylamino)-3-phenylpropionyloxy}benzyl]-3,5-dimethylbenzoate, methyl (S)-4-[5-(1-imidazolyl)-2-methyl-α-{(S)-2-(4-methylbenzenesulfonylamino)-3-phenylpropionyloxy}benzyl]-3,5-dimethylbenzoate, methyl (±)-4-[5-(1-imidazolyl)-2-methyl-α-{(S)-2-(4-methylbenzenesulfonylamino)propionyloxy}benzyl]-3,5-dimethylbenzoate, and methyl (S)-4-[5-(1-imidazolyl)-2-methyl-α-{(S)-2-(4-methylbenzenesulfonylamino)propionyloxy}benzyl]-3,5-dimethylbenzoate, an optically active compound thereof or a pharmaceutically acceptable salt thereof.

6. A method for producing a compound of the formula (I)

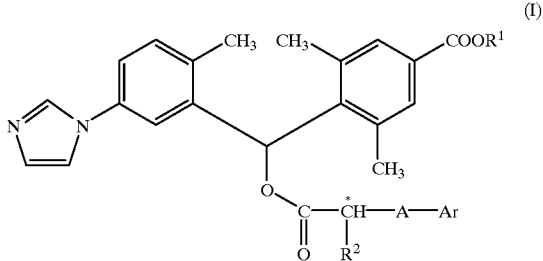
(I)

wherein $R^1$ is a lower alkyl, a phenylalkyl or a substituted phenylalkyl;

$R^2$ is a lower al, a phenylalkyl or a substituted phenylalkyl;

Ar is a phenyl, a substituted phenyl, a naphthyl, a substituted naphthyl, a thienyl, a substituted thienyl, a furyl, a substituted furyl, a pyridyl or a substituted pyridyl;

A is a single bond or —$NHSO_2$—; and the carbon atom marked with * shows (S)— or (R)—, which comprises reacting a compound of the formula (III)

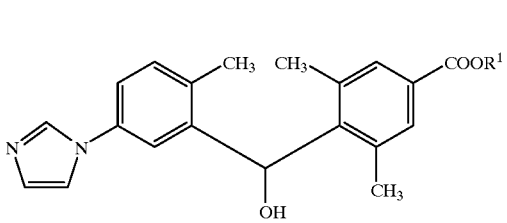
(III)

wherein $R^1$ is a lower alkyl, a phenylalkyl or a substituted phenylalkyl, and a compound of the formula (IV)

(IV)

wherein $R^2$ is a lower alkyl, a phenylalkyl or a substituted phenylalkyl;

Ar is a phenyl, a substituted phenyl, a naphthyl, a substituted naphthyl, a thienyl, a substituted thienyl, a furyl, a substituted furyl, a pyridyl or a substituted pyridyl;

A is a single bond or —$NHSO_2$—; and the carbon atom marked with * shows (S)— or (R)—, or reactive derivative selected from the group consisting of acid halides, acid anhydrides and active esters thereof.

7. The method of claim 6, wherein, in the formula (I), $R^1$ is a lower alkyl.

8. The method of claim 6, wherein, in the formula (I), Ar is phenyl, substituted phenyl, naphthyl or substituted naphthyl.

9. The method of claim 6, wherein, in the formula (I), $R^1$ is a lower alkyl, $R^2$ is a lower alkyl, a phenylalkyl or a substituted phenylalkyl, Ar is a phenyl, a substituted phenyl, a naphthyl or a substituted naphthyl, and A is a single bond or —$NHSO_2$—.

10. The method of claim 6, wherein the compound of the formula (I) is a ember selected from the group consisting of methyl (±)-4-[5-(1-imidazolyl)-α-{(S)-2-(6-methoxy-2-naphthyl)propionyloxy}-2-methylbenzyl]-3,5-dimethylbenzoate, methyl (S)-4-[5-(1-imidazolyl)-α-{(S)-2-(6-methoxy-2-naphthyl)propionyloxy}-2-methylbenzyl]-3,5-dimethylbenzoate, methyl (R)-4-[5-(1-imidazolyl)-α-{(S)-2-(6-methoxy-2-naphthyl)propionyloxy}-2-methylbenzyl]-3,5-dimethylbenzoate, methyl (±)-4-[5-(1-imidazolyl)-α-{(S)-2-(4-chlorobenzenesulfonylamino)propionyloxy}-2-methylbenzyl]-3,5-dimethylbenzoate, methyl (S)-4-[5-(1-imidazolyl)-α-{(S)-2-(4-chlorobenzenesulfonylamino)propionyloxy}-2-methylbenzyl]-3,5-dimethylbenzoate, methyl (±)-4-[5-(1-imidazolyl)-2-methyl-α-{(S)-2-(4-methylbenzenesulfonylamino)-3-phenylpropionyloxy}benzyl]-3,5-dimethylbenzoate, methyl (S)-4-[5-(1-imidazolyl)-2-methyl-α-{(S)-2-(4-methylbenzenesulfonylamino)-3-phenylpropionyloxy}benzyl]-3,5-dimethylbenzoate, methyl (±)-4-[5-(1-imidazolyl)-2-methyl-α-{(S) -2-(4-methylbenzenesulfonylamino)propionyloxy}benzyl]-3,5-dimethylbenzoate, and methyl (S)-4-[5-(1-imidazolyl)-2-methyl-α-{(S)-2-(4-methylbenzenesulfonylamino)propionyloxy}benzyl]-3,5-dimethylbenzoate.

* * * * *